(12) United States Patent
Halsne

(10) Patent No.: US 11,103,719 B2
(45) Date of Patent: Aug. 31, 2021

(54) METHOD AND APPARATUS FOR NON-AUDIBLE SENSING OF A DEFIBRILLATOR STATUS INDICATOR

(71) Applicant: KONINKLIJKE PHILIPS N.V., Eindhoven (NL)

(72) Inventor: Eric Grant Halsne, Kenmore, WA (US)

(73) Assignee: Koninklijke Philips N.V., Eindhoven (NL)

(*) Notice: Subject to any disclaimer, the term of this patent is extended or adjusted under 35 U.S.C. 154(b) by 591 days.

(21) Appl. No.: 16/068,908

(22) PCT Filed: Jan. 10, 2017

(86) PCT No.: PCT/EP2017/050393
§ 371 (c)(1),
(2) Date: Jul. 10, 2018

(87) PCT Pub. No.: WO2107/121718
PCT Pub. Date: Jul. 20, 2017

(65) Prior Publication Data
US 2019/0015672 A1      Jan. 17, 2019

Related U.S. Application Data

(60) Provisional application No. 62/277,231, filed on Jan. 11, 2016.

(51) Int. Cl.
*A61N 1/39*      (2006.01)
*A61N 1/372*     (2006.01)
*G01N 29/12*     (2006.01)

(52) U.S. Cl.
CPC ....... *A61N 1/3993* (2013.01); *A61N 1/37217* (2013.01); *A61N 1/37282* (2013.01);
(Continued)

(58) Field of Classification Search
CPC .............. A61N 1/3993; A61N 1/37217; A61N 1/37282; A61N 1/3931; G01N 29/12;
(Continued)

(56) References Cited

U.S. PATENT DOCUMENTS

| 4,614,192 A | 9/1986 | Imran et al. |
| 6,148,233 A | 11/2000 | Owen et al. |

(Continued)

FOREIGN PATENT DOCUMENTS

| CN | 2928126 Y | 8/2007 |
| EP | 1425934 B1 | 8/2007 |

(Continued)

OTHER PUBLICATIONS

Mendel Kleiner: "Electroacoustics"; 2013 pp. 445-446, Part 23.3.5, Diaphragm Motion Feedback.

*Primary Examiner* — Catherine M Voorhees
*Assistant Examiner* — Roland Dinga

(57) ABSTRACT

A monitoring device for monitoring the readiness state of an automated external defibrillator (AED) and communicating the state to a remote receiver is described. An associated method is described as well. The monitoring device captures a non-acoustic parameter related to the activation of the AED readiness state beeper.

18 Claims, 6 Drawing Sheets

AED and communicator

(52) U.S. Cl.
CPC ........... *A61N 1/3931* (2013.01); *G01N 29/12* (2013.01); *G01N 2291/014* (2013.01); *G01N 2291/028* (2013.01); *G01N 2291/0237* (2013.01); *G01N 2291/02863* (2013.01); *G01N 2291/02881* (2013.01)

(58) Field of Classification Search
CPC ..... G01N 2291/014; G01N 2291/0237; G01N 2291/028; G01N 2291/02863; G01N 2291/02881
See application file for complete search history.

(56) References Cited

U.S. PATENT DOCUMENTS

| | | | |
|---|---|---|---|
| 6,397,104 | B1 | 5/2002 | Miller et al. |
| 6,727,814 | B2 | 4/2004 | Saltzstein et al. |
| 6,871,093 | B2 | 3/2005 | Hansen |
| 8,081,071 | B1 * | 12/2011 | Vaisnys ................. G16H 40/67 340/539.12 |
| 2004/0019258 | A1 * | 1/2004 | Kavounas ............ A61N 1/3904 600/300 |
| 2004/0184623 | A1 | 9/2004 | Johannsen et al. |
| 2005/0219228 | A1 | 10/2005 | Alameh et al. |
| 2006/0079793 | A1 | 4/2006 | Mann et al. |
| 2006/0142806 | A1 * | 6/2006 | Katzman .............. A61N 1/3904 607/5 |
| 2010/0106028 | A1 | 4/2010 | Penner et al. |
| 2011/0029041 | A1 * | 2/2011 | Wiskerke ............. H04R 25/606 607/57 |
| 2012/0105238 | A1 | 5/2012 | Caby et al. |
| 2015/0321020 | A1 * | 11/2015 | Gumbrell ............ A61N 1/3925 607/5 |
| 2015/0343229 | A1 | 12/2015 | Peterson et al. |
| 2017/0157416 | A1 * | 6/2017 | Medema ................ A61N 1/046 |

FOREIGN PATENT DOCUMENTS

| | | |
|---|---|---|
| RU | 2012113293 A | 10/2013 |
| WO | 2008116822 A2 | 10/2008 |
| WO | 2014033605 A1 | 3/2014 |

* cited by examiner

AED and communicator

METHOD AND APPARATUS FOR NON-AUDIBLE SENSING OF A DEFIBRILLATOR STATUS INDICATOR

CROSS-REFERENCE TO PRIOR APPLICATIONS

This application is the U.S. National Phase application under 35 U.S.C. § 371 of International Application No. PCT/EP2017/050393, filed on Jan. 10, 2017, which claims the benefit of U.S. Provisional Patent Application No. 62/277,231, filed on Jan. 11, 2016. These applications are hereby incorporated by reference herein.

BACKGROUND

The invention relates to an improved apparatus and method for maintaining an automated external defibrillator (AED). In particular, the invention pertains to a monitoring device which captures a state of readiness of a co-located AED, and subsequently communicates the state to a remote service provider location.

FIG. 1 illustrates a prior art AED 100 is shown in a top perspective view. The AED 100 is housed in a rugged polymeric case 102 which protects the electronic circuitry inside the case and also protects the layperson user from shocks. Such AEDs are generally mounted in distinctive locations such as on walls in high traffic areas and with signage to mark and indicate their locations, or the AED may be placed anywhere in the home. A home AED, like other AEDs, may go an extended period of time without use, and so it may be stored in a location lacking prominence such as in a closet or drawer.

Attached to the case 102 by electrical leads is a pair of electrode pads. In the embodiment of FIG. 1 the electrode pads are in a sealed airtight cartridge 104 located in a recess on the top side of the AED 100. The electrode pads are accessed for use by pulling up on a handle 108 which allows removal of a plastic cover over the electrode pads. A small ready light 106 informs the user of the readiness of the AED. In this embodiment the ready light blinks after the AED has been properly set up and is ready for use. The ready light is on constantly when the AED is in use, and the ready light is off when the AED needs attention.

Below the ready light is an on/off button 110. The on/off button is pressed to turn on the AED for use. To turn off the AED a user holds the on/off button down for one second or more. A caution light 114 flashes when information is available for the user. The user depresses the information button to access the available information. A caution light 114 blinks when the AED is acquiring heartbeat information from the patient and lights continuously when a shock is advised, alerting the rescuer and others that no one should be touching the patient during these times. Interaction with the patient while the heart signal is being acquired can introduce unwanted artifacts into the detected ECG signal. A shock button 116 is depressed to deliver a shock after the AED informs the rescuer that a shock is advised. An infrared port 118 on the side of the AED is used to transfer data between the AED and a computer. This data port find used after a patient has been rescued and a physician desires to have the AED event data downloaded to his or her computer for detailed analysis.

A speaker 120 provides voice instructions to a rescuer to guide the rescuer through the use of the AED to treat a patient. A beeper 122 is provided which "chirps" when the AED needs attention such as electrode pad replacement or a new battery. The annunciator includes a vibrating diaphragm to generate acoustic energy. An exemplary type of annunciator is a piezo-electric disk beeper such as the 5V audio transducer EMX-7T05SCL63, manufactured by the Myn Tahl Corporation of Fremont Calif. Of course, beeper 122 requires AED battery power to operate.

FIG. 2 illustrates a typical Beep Sequence 202 which issues from an AED beeper 122 as a result of an audible fault alert 200 that is discovered during a device self-test. After the fault is detected, AED 100 drives the beeper 122 to issue a series of beep 204 that are 125 mS long, separated by a beep interval 206 of about 875 mS. The beep frequency in this example is 2400 Hz. Beep Sequence 202 is three "chirps", which indicates a fault that renders the device "not ready for use." In the case of faults which require a user's attention but that are not serious enough to render the device inoperable, such as a mild low battery condition, the beep sequence may be just one "chirp." The beep sequence is repeated every 8 seconds until either the fault is corrected or until the battery dies.

Other AEDs may have different beep sequences, frequencies, and repetition intervals. In all cases, however, the particular sequence unambiguously indicates a self-test fault and is of a pre-determined and known acoustic signature.

One problem in the prior art is that the self-test fault alerting is local. If a user is not within visual or audible range of the AED when it begins to issue an alert, then corrective action is not possible. If the alert continues until the AED battery is depleted, then it is further possible that the device will not be ready to use when needed. Thus, unnecessary delay to treatment of a cardiac arrest victim may ensue.

BRIEF SUMMARY

AEDs which incorporate a communications module for reporting a fault have not yet been successful in the market place. The power required by existing communications circuits has tended to reduce the standby life of the AED battery to unacceptable levels. Whereas many AED batteries are intended to function for a year or longer in standby use, such batteries quickly deplete when supplying power to even low-power communications circuits. What is needed, therefore, is a separate monitoring system which can remotely monitor an AED readiness indicator and provide a remote notification. The separate monitoring system should be arranged with an independent power supply, either easily changed or re-charged, and also should be arranged to consume as little power as possible. In addition, the inventors have recognized that sensors which can detect non-audible characteristics of an activated acoustic readiness indicator may enable very low-power detection of a local AED self test fault alert. Such sensors can also avoid "cross-detection" of alerts arising from AEDs within audible range of the sensor.

Accordingly, the inventors describe an apparatus and method to overcome the problems with the prior art AEDs by describing a device, preferably located adjacent to an AED storage location, that monitors the status of the AED and communicates that status to a remote location. In some embodiments, a monitoring device for sensing an operating status of a defibrillator having an audible annunciator with a diaphragm may include a sensor disposed adjacent the annunciator and operable to detect a non-audible parameter related to a motion of the diaphragm, a hardware processor in electrical communication with the sensor, and/or an output in communication with the hardware processor for providing a signal indicative of the diaphragm motion.

In some embodiments, the sensor which detects the non-audible parameter may be one or more of a capacitive sensor, an optical sensor, and a temperature sensor disposed to detect the diaphragm motion. In other embodiments, a decal is placed on the AED case adjacent the annunciator. One of the above-mentioned sensor technologies and/or an accelerometer may be disposed to sense a vibration of the AED case that is induced by the diaphragm motion.

A method for sensing an operating status of a defibrillator having an audible annunciator with a diaphragm is also described.

In some embodiments, a method of sensing an operating status of a defibrillator having an audible annunciator with a diaphragm may include providing a monitoring device disposed adjacent the defibrillator, sensing with the monitoring device a motion of the annunciator diaphragm, and/or generating an output signal corresponding to the sensing step.

In some embodiments, the monitoring device may include a sensor disposed adjacent the annunciator and operable to detect a non-audible parameter related to a motion of the diaphragm, a hardware processor in electrical communication with the sensor, and an output in communication with the hardware processor for providing a signal indicative of the diaphragm motion.

In some embodiments, such a method may further include a step of comparing the motion from the sensing step with a known characteristic of the annunciator diaphragm.

In some embodiments, the generating step occurs responsive to the comparing step.

In some embodiments, the known characteristic is one of a diaphragm operating frequency, a diaphragm operating duration, and a temperature change resulting from a diaphragm operation.

In some embodiments, such a method may further include a step of transmitting a wireless communications signal from the monitoring device to a remote receiver responsive to the generating step.

In some embodiments, such a method may further include activating the monitoring device on a predetermined schedule prior to the sensing step and/or entering a low-power standby mode of operation after the sensing step.

As used herein for purposes of the present disclosure, the term "processor" is used generally to describe various apparatus relating to the operation of a ventilator apparatus, system, or method. A processor can be implemented in numerous ways (e.g., such as with dedicated hardware) to perform various functions discussed herein. A processor is also one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more computer storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

In various implementations, the terms "low-power standby circuit", "clock", "state change monitor", "comparator" apply to components that are generally known in the art, and may be embodied in conventional microprocessors, application specific integrated circuits (ASICs), and field-programmable gate arrays (FPGAs), or may be integrated into the above described processor or controller. "Outputs" and "signals" may be understood to be electrical or optical energy impulses which represent a particular detection or processing result.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
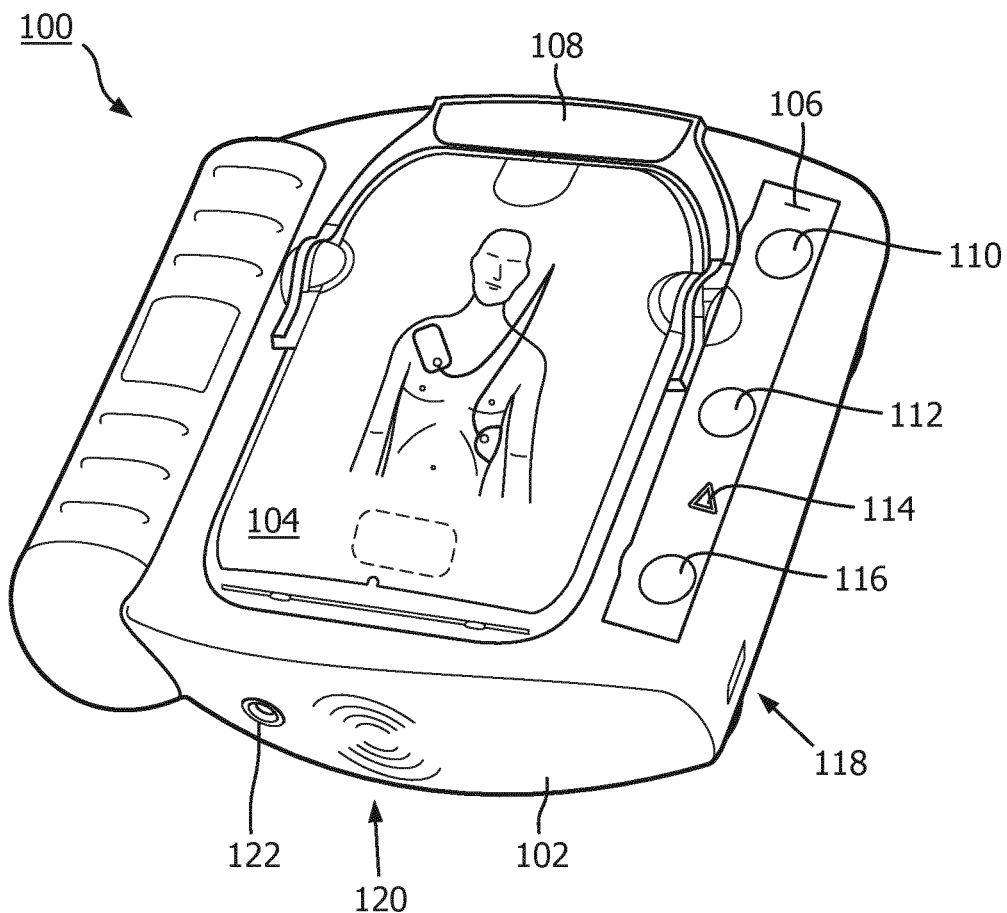
FIG. 1 illustrates a prior art AED shown in a top perspective view.
Figure 2:
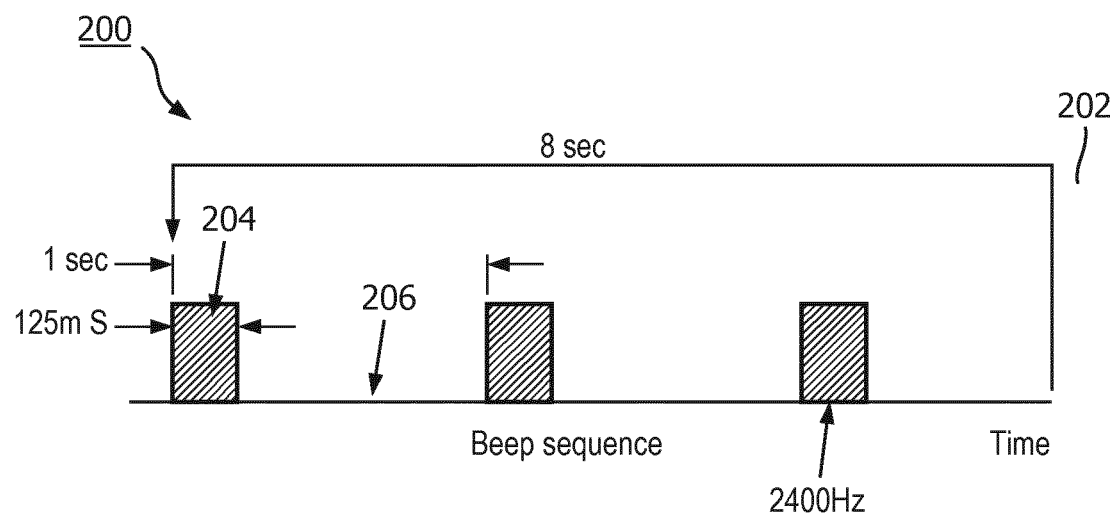
FIG. 2 illustrates an exemplary audible alert sequence from a prior art AED.

The phrases "in one embodiment", "in various embodiments", "in some embodiments", and the like are used repeatedly. Such phrases do not necessarily refer to the same embodiment. The terms "comprising", "having", and "including" are synonymous, unless the context dictates otherwise.

Reference is now made in detail to the description of the embodiments as illustrated in the drawings. While embodiments are described in connection with the drawings and related descriptions, there is no intent to limit the scope to the embodiments disclosed herein. On the contrary, the intent is to cover all alternatives, modifications and equivalents. In alternate embodiments, additional devices, or combinations of illustrated devices, may be added to or combined, without limiting the scope to the embodiments disclosed herein.

Figure 3:
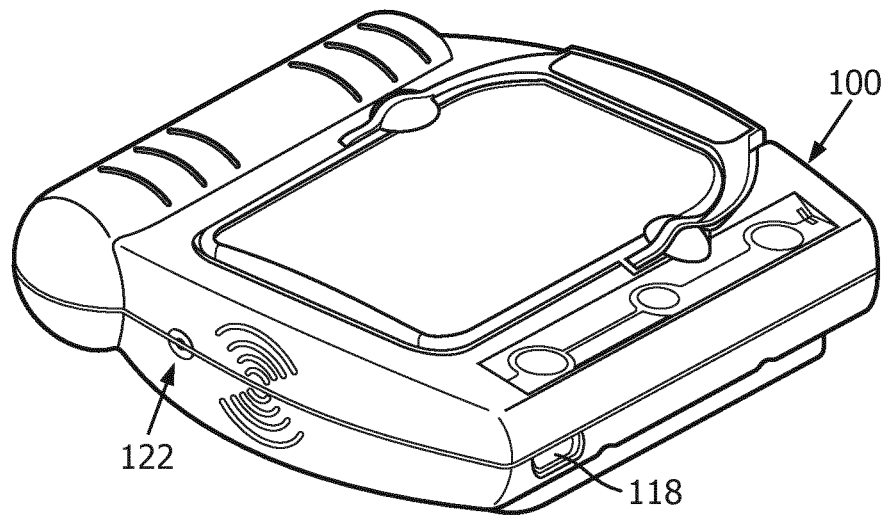
FIG. 3 illustrates an exemplary monitoring device for sensing an operating status of a defibrillator having an audible annunciator with a diaphragm, in accordance with one embodiment of the invention.
Figure 3:
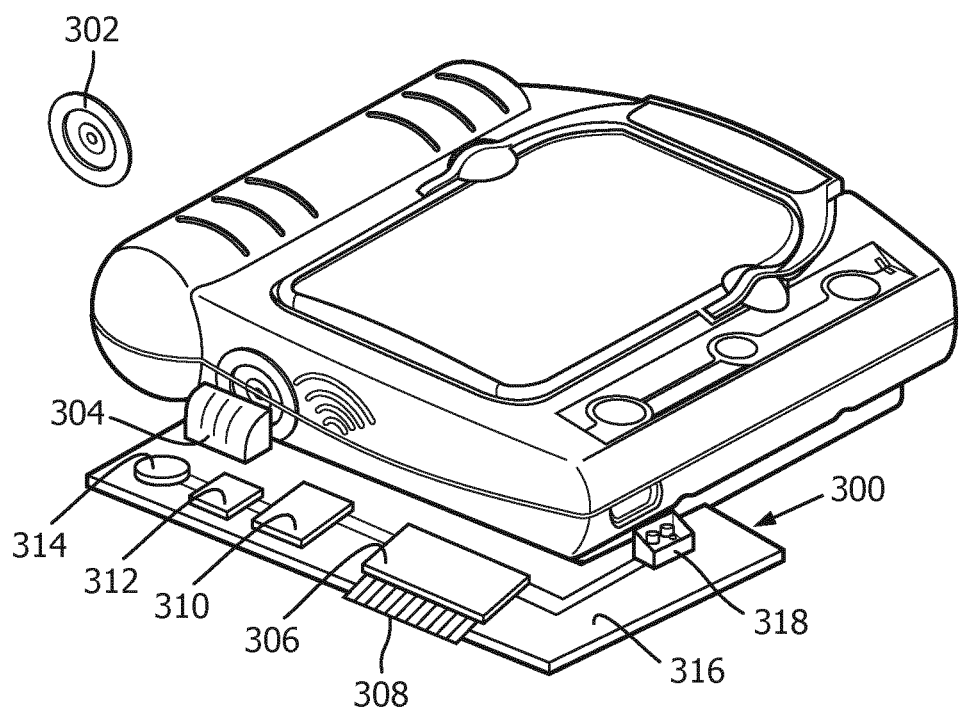

FIG. 3 illustrates an exemplary monitoring device 300 for sensing the operating status of a defibrillator or AED 100, in accordance with one embodiment. As previously described, AED 100 includes an audible annunciator 122 with a vibrating diaphragm. AED 100 may also include infrared port 118.

Monitoring device 300 for sensing an operating status of AED 100 is shown in a preferred position disposed adjacent the defibrillator. The disposition is such that a sensor 304 is disposed adjacent the annunciator. Sensor 304 in particular is of a type that is operable to detect a non-audible parameter that is related to the motion of the vibrating diaphragm in the annunciator. Monitoring device 300 includes a hardware processor 306 that is disposed in communication with sensor 304. When sensor 304 provides an input to the hardware processor 306 relating to an actuation of the annunciator, processor 306 issues a signal at output 308 that corresponds to the detection. As will be described, output 308 is preferably provided to a wireless transmitter that is operable to transmit a corresponding defibrillator status report to a remote receiver.

Also shown on monitoring device 300 is a low-power standby circuit 310, clock 312 and power supply 314 in communication with the hardware processor 306. These components enable the monitoring device 300 to operate for extended periods, e.g. months, without an external power source, by placing the monitoring device 300 in a low-power standby mode for most of the time. The clock 312 drives the standby circuit 310 to activate hardware processor 306 on a predetermined periodicity, and for a brief predetermined time. The activation interval is selected such that the interval that will capture any annunciator-induced vibration if there is one.

Components for the monitoring device 300 are disposed on one or more substrate 316, such as a printed circuit board.

Also shown is an optional decal 302 that is arranged to be applied to the AED 100 around or next to the annunciator. The decal is selected to be used to increase the sensitivity of sensor 304 to annunciator-induced vibration. Hence, the decal 302 may be electrically conductive if the sensor 304 is sensitive to electrical changes induced by the diaphragm motion, or may be optically reflective if the sensor 304 is sensitive to vibrational, reflective, or positional changes induced by the diaphragm motion. Decal 302 preferably is adhesively applied to the AED 100.

Not shown in FIG. 3 for ease of viewing the components is an enclosure for monitoring device 300 that surrounds at least one side of AED 100. The enclosure is preferably integrated with the AED 100 carrying case or the wall mount.

Figure 4:
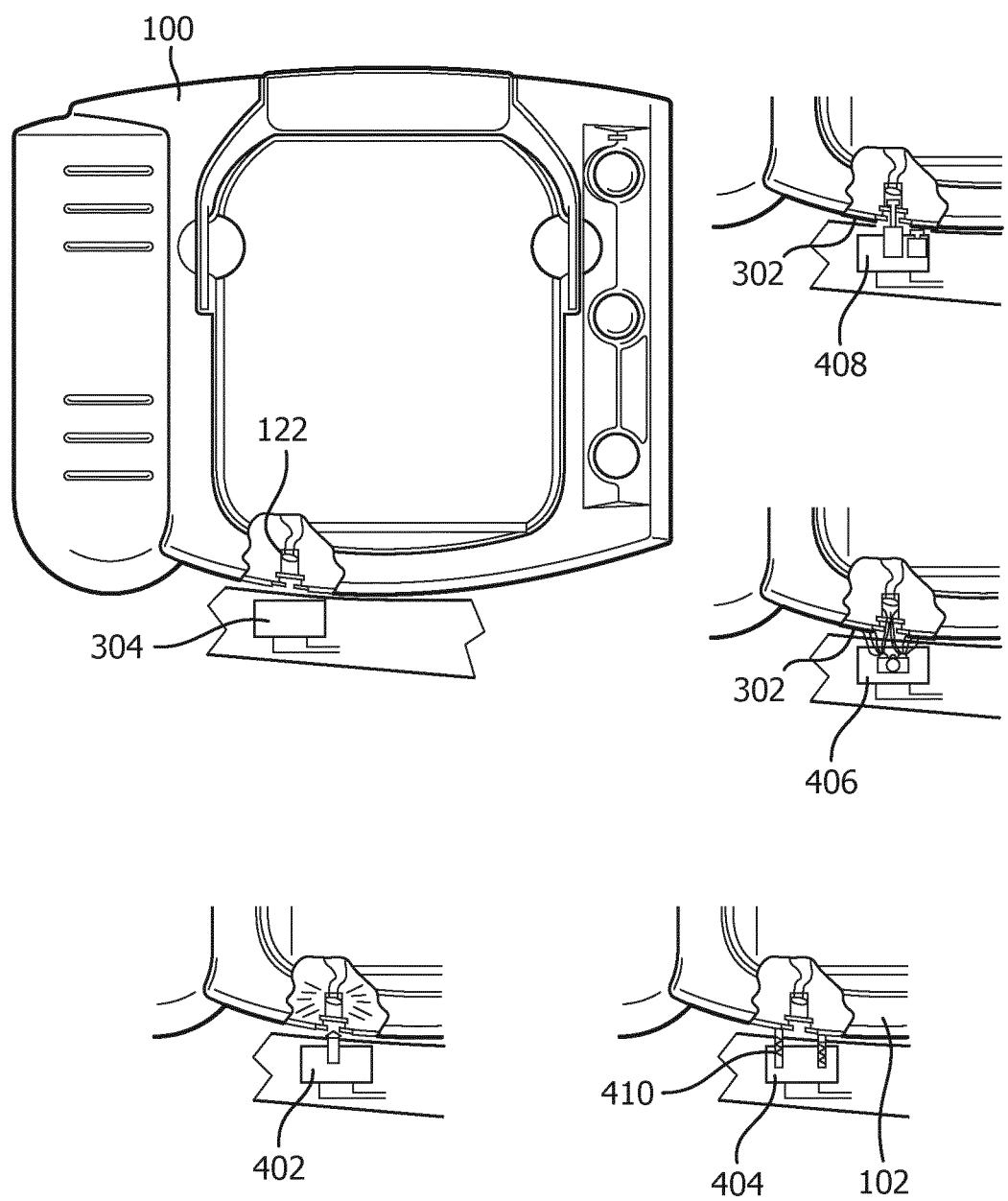
FIG. 4 illustrates several alternative embodiments of a sensor in an AED monitoring device.

FIG. 4 illustrates several alternative embodiments of a sensor operable to detect a non-audible parameter from an AED 100 annunciator activation. Sensor 304 may be one of several technologies as part of the monitoring device 300. It is understood that circuitry and processing by hardware processor 306 may differ somewhat between technologies, but also falls within the scope of the invention.

Sensor 304 may be a temperature sensor 402. It is known that beeper 122 heats slightly during activation, the temperature change being induced by the rapid vibratory motion of the annunciator diaphragm. Therefore, temperature sensor 402 is arranged closely adjacent to the beeper 122 diaphragm, and is selected with sufficient sensitivity to detect a pre-determine temperature change over a time interval that corresponds to the known "chirp" or series of chirps. Hardware processor 306 processes the corresponding signal, for example by comparing a known temperature response of the beeper 122 during a "chirp" or Beep Sequence 202 to the sensor signal. If the comparing step is a match, then a diaphragm motion of the beeper 122 is indicated. Hardware processor 306 then provides a corresponding signal to the output.

Alternatively, sensor 304 may be a vibration sensor 404. One embodiment of vibration sensor 404 is an accelerometer which is mounted on the printed circuit assembly, or one that is integrated with the hardware processor 306. Vibration sensor 404 is arranged to detect vibrations induced on the AED case 102 and enabled by the case 102 coupling with beeper 122. In this embodiment, hardware processor 306 compares a sensed frequency, duration and/or repetition pattern of vibrations to known parameters to determine whether the annunciator has activated.

Vibrational coupling of vibration sensor 404 with AED case 102 may optionally be improved by arranging a shorting coupler 410 between vibration sensor 304 and case 102. Shorting coupler 410 is preferably arranged to rest against case 102 when installed with monitoring device 300. Shorting coupler 410 may be hard "whiskers", prongs or other devices known to provide good vibrational coupling between objects.

Alternatively, sensor 304 may be an optical sensor 406. Optical sensor 406 preferably includes a light which illuminates either the annunciator diaphragm or an optically reflective surface on case 102. A photosensitive detector in optical sensor 304 is arranged to capture the reflected light and generate a corresponding electrical output signal. Optical sensor 406 thus detects any change in reflectance caused by changes in the diaphragm position during the diaphragm motion. One example of an optical sensor 406 is an LED laser diode-based optical transceiver, which includes both a laser diode light and a photo-sensor that is attuned to the laser diode frequency for enhanced sensitivity and noise suppression.

An alternative arrangement includes an optically reflective decal 302 that may be applied around beeper 122 such that optical sensor 406 detects changes in the decal 302 position induced by the annunciator-induced vibrations coupled to case 102. Thus, the positioning of the optical sensor 406 relative to the annunciator diaphragm is not so sensitive.

Alternatively, sensor 304 may be a capacitive sensor 408 which senses motion of the annunciator diaphragm that indicates activation. Capacitive sensor 408 may be disposed in one of three ways. If sensitive enough, capacitive sensor 408 may be located directly over the annunciator port in AED case 102. Alternatively, capacitive sensor 408 may be disposed on the end of a flexible stem which extends into the case 102 port hole to place the capacitive sensor 408 closer to the diaphragm. Alternatively, an electrically conductive decal may be applied to the defibrillator surface adjacent the annunciator. Capacitive sensor 408 is then disposed adjacent the decal, and can thus detect an annunciator-induced vibration of the AED 100 surface.

Figure 5:
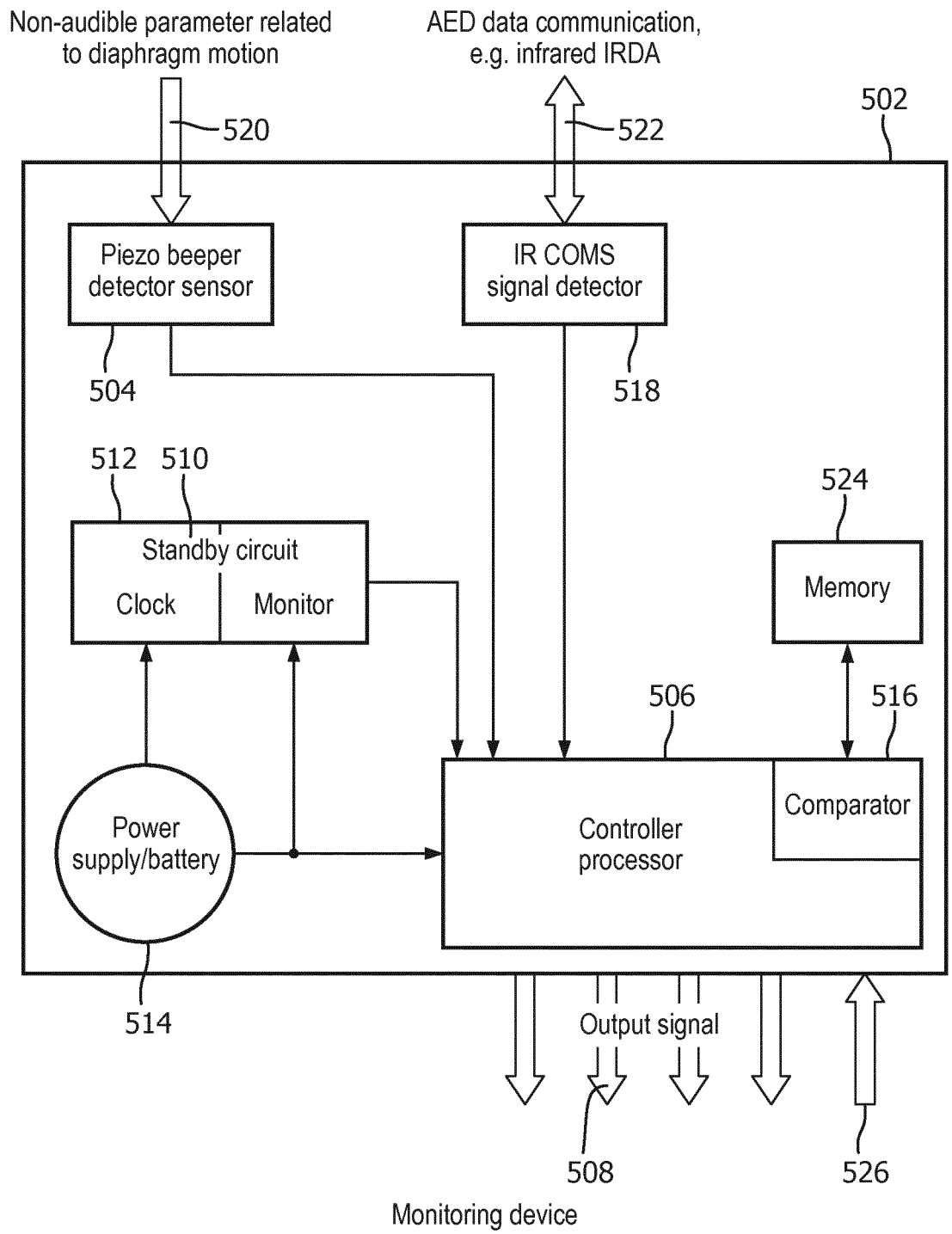
FIG. 5 illustrates an exemplary block diagram of the monitoring device for sensing an operating status of a defibrillator, the defibrillator having an audible annunciator with a diaphragm.

FIG. 5 illustrates an exemplary block diagram of the monitoring device for sensing an operating status of a defibrillator, the defibrillator having an audible annunciator with a diaphragm. monitoring device 502 includes several elements. Although shown as functional blocks, each element is enabled by structure such as circuitry interconnected on a substrate by wire traces, semi-conductor processors and memory, and sensing devices. The elements may be controlled by software instructions residing in memory and being executed in one or more of the processors.

Monitoring device 502 obtains an input indicating the activation of the associated AED 100 annunciator at diaphragm motion parameter 520, which is a non-audible related parameter. Sensor 504, of a type previously described, captures the input. Sensor 504 passes the signal via electrical communication to the hardware processor 506. Hardware processor 506 analyzes the signal, and if the analysis indicates a signal corresponding to diaphragm motion, the processor provides an output 508.

Signal analysis may be conducted with a comparator 516 and a computer storage memory 524, consisting of a non-transitory medium or the like. Memory 524 stores data corresponding to a known characteristic of the annunciator, such as the aforementioned frequency, duration, repetition rate data, and known temperature and heating profiles. Comparator 516 compares the characteristics profile to the received parameter. Correlation within a detection threshold indicates a signal corresponding to diaphragm motion. Optionally, hardware processor 506 may store data indicative of the detected diaphragm motion, such as number of chirps, type of alert detected, and a cumulative number of chirps or operations of the diaphragm detected, into memory 524 for later use in diagnostics and trouble-shooting.

Also included in monitoring device 502 is a low-power standby circuit 510 which may include a clock 512 and a state change monitor. The standby circuit 510 maintains the monitoring device 502 in a very low-power standby mode of operation in order to maximize the life of the monitoring device 502 battery 514. Preferably, clock 512 activates the standby circuit 510 for a predetermined time duration on a predetermined schedule that corresponds to a self-testing periodicity of the AED 100. Thus, the monitoring device 502 is active only for those periods when AED 100 is also active and performing its self-test. After monitoring device 502 ascertains the status of the AED 100, and passes any necessary notifications to output 508, standby circuit 510 returns the hardware processor 506 to the low-power standby mode of operation.

Also included in monitoring device 502 is an optional second sensor 518 which is in communication with hardware processor 506. Second sensor 518 is disposed adjacent AED 100 such that it is operable to sense an AED data signal 522 output from the defibrillator. The data communication may be from wireless RF, so second sensor 518 may be a Wi-Fi, Near Field Communication (NFC), Bluetooth™ receiver or the like. The data communication might also be optical, such as from infrared data communication (IRDA), so second sensor 518 may be an IrDA receiver. Standby circuit 510 may optionally be triggered to activate hardware processor 506 based on a detected AED data signal 522. Because the AED data signal 522 is typically transmitted when the AED 100 activates, hardware processor 506 may adjust the predetermined periodicity and the timing of the next wake-up activation based on this sensed wireless data communication.

A communicator signal 526 may optionally be included as another input to monitoring device 502. This data pathway may enable to monitoring device 502 to further adjust itself or the AED 100 via AED data signal 522 based on a communication from a remote provider. For example, communicator signal 526 may signal hardware processor 506 to transmit all collected maintenance data held within memory 524.

Figure 6:
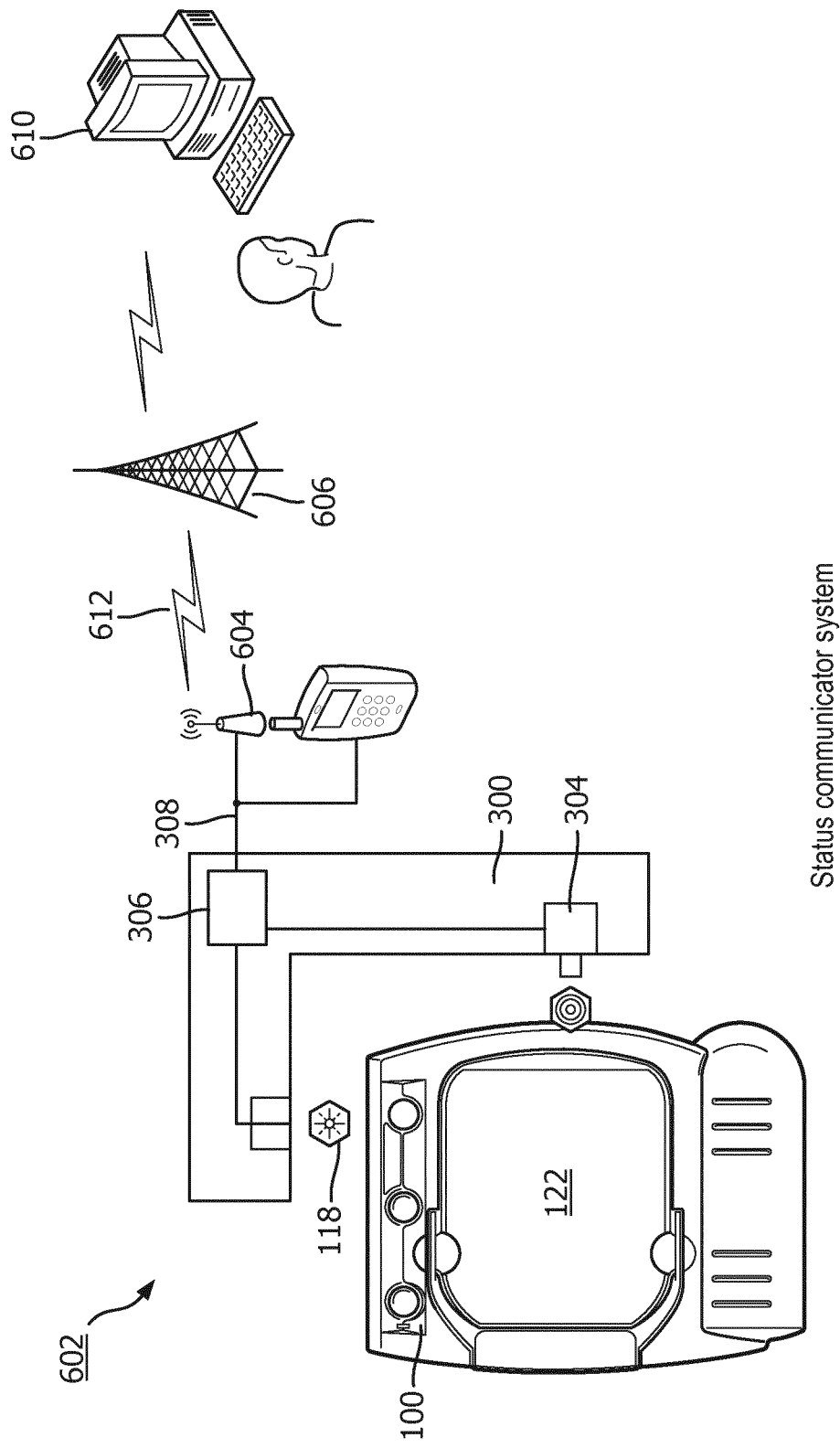
FIG. 6 illustrates a system for maintaining a defibrillator from a remote location, in accordance with one embodiment.

FIG. 6 illustrates a Status Communicator System 602 for maintaining a defibrillator from a remote location, in accordance with one embodiment of the invention. The system comprises four main components in addition to the monitored defibrillator or AED 100. The monitoring device 300, as previously described, includes a sensor 304 that is operable to detect a non-audible parameter related to the motion of a beeper 122 diaphragm. Sensor 304 sends a signal to hardware processor 306 which in turn provides a status signal via output 308 to a wireless transmitter 604.

Wireless transmitter 604 is the second component of the Status Communicator System 602. Preferably, wireless transmitter 604 is a standard communication device such as a smartphone or a Wi-Fi network node, the device adapted to include means for receiving an input from monitoring device 300. The input means may be a USB cable, a custom hardwire ribbon cable, a NFC/Bluetooth™ wireless connection, or a similar interface. Wireless transmitter 604 preferably maintains its own power supply, and has software which executes instructions to transmit defibrillator status information on a periodic or as-needed basis. Accordingly, 604 transmits a defibrillator status report transmission 612 over a third component wireless network 606 to a fourth component remote receiver 610. There, a service provider can take any needed corrective action, such as contacting the AED 100 owner or initiating a service call. Optionally, the Status Communicator System 602 may be bi-directional so that the 610 may transmit a reply message back to 604 for display on a screen associated with the wireless transmitter 604, monitoring device 300, or AED 100. The return message may also be a control signal which changes the status of AED 100 or monitoring device 300 to accommodate the nature of the detected failure.

Figure 7:
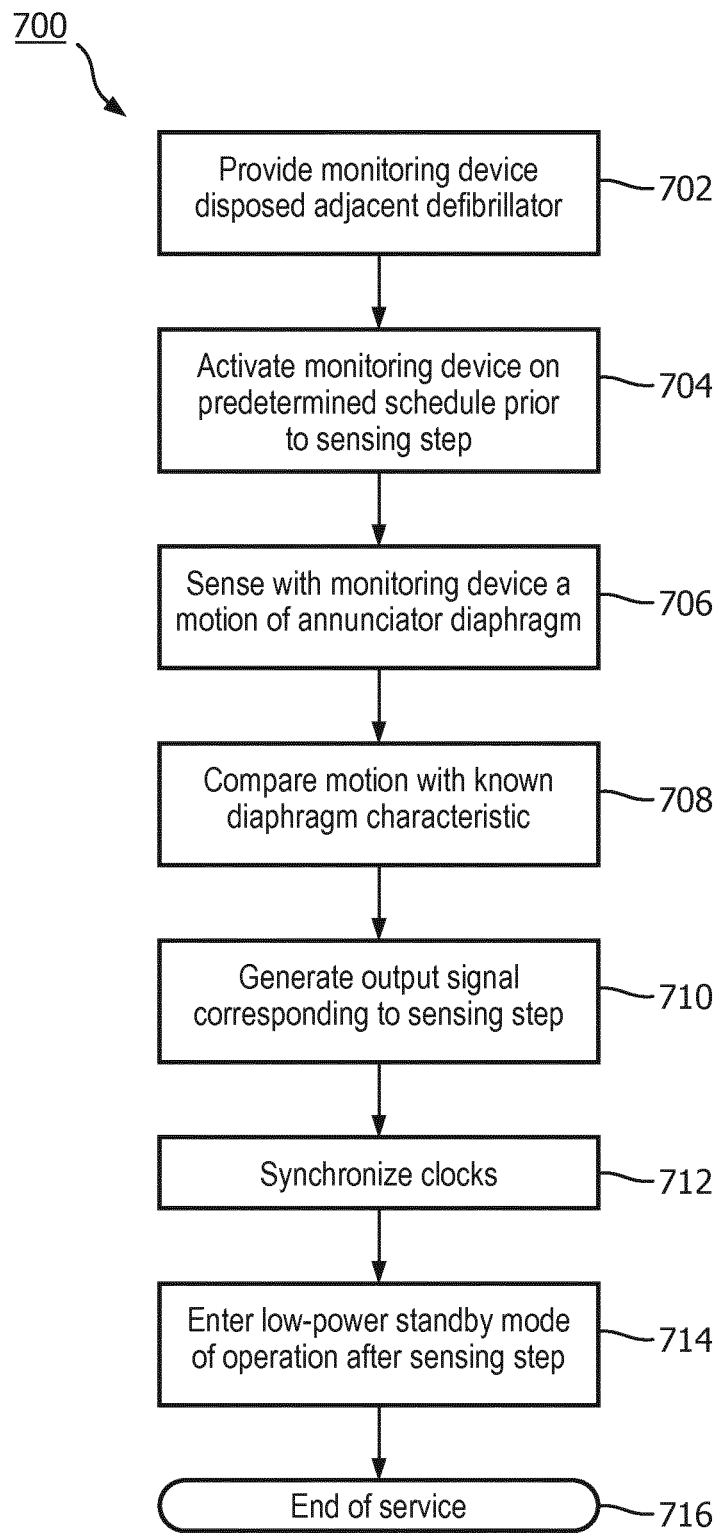
FIG. 7 illustrates a method for monitoring an AED 100 in accordance with one embodiment.

FIG. 7 illustrates a method of sensing an operating status of a defibrillator having an audible annunciator with a diaphragm 700. The method 700 begins with a providing step 702 of providing a monitoring device according to the present inventive apparatus, wherein the monitoring device is preferably disposed adjacent the defibrillator, including as an integral part of the defibrillator storage case or wall mount. The monitoring device 300 is placed into service, preferably in a low-power standby mode, and begins to operate according to a predetermined schedule. Monitoring device 300 may be synchronized with AED 100 at this step, either manually or automatically, for example by activating immediately and remaining activated until the monitoring device 300 senses the next AED 100 activation, after which both devices re-enter a low-power standby mode of operation.

At step 704, the monitoring device 300 activates itself. The preferred method of activation is according to a predetermined schedule or periodicity. The schedule and periodicity is even more preferably corresponding to a known self-testing periodicity of AED 100. Alternatively, the monitoring device 300 may activate on a multiple of the AED 100 self-testing periodicity, such as every two or three periodic self-tests, in order to further conserve monitoring device 300 battery power. In order to maintain synchronization between monitoring device 300 and AED 100, the monitoring device 300 clock may be adjusted at an activation to match the AED 100 timer.

In sensing step 706, the activated monitoring device senses a motion of the adjacent AED 100 annunciator, according to one of the embodiments of the previous apparatus description. For example, the sensing step 706 may be an optical or capacitive sensing of the diaphragm motion, a temperature excursion in the annunciator induced by activation, or a sensing of mechanical vibration of the AED 100 case induced by the annunciator. A lack of sensing within a predetermined time during the cause the method to either proceed to a corresponding output step 710, or re-enter the low-power standby mode at step 714 until the next scheduled activation.

At optional comparing step 708, a characteristic of the sensed motion from sensing step 706 is compared to a known characteristic of the activated annunciator diaphragm, by one of the methods as previously described. If the hardware processor 306 in comparing step 708 determines a match, then an activation is indicated to the generating step 710.

Generating step 710 generates an output signal corresponding to sensing step 706 and/or comparing step 708. An output signal is preferably provided by the monitoring device 300 to an associated wireless transmitter 604 which in turn sends a corresponding wireless communications signal to a remote receiver. Alternatively, the output signal is provided to computer storage memory 524 to maintain a record of the operating performance, or to allow signals to be deferred to save system power or to reduce nuisance alarms.

Optional synchronizing step 712 is conducted by the monitoring device 300 before it returns to a low-power standby mode of operation. In this step, monitoring device 300 adjusts its next "wake-up" activation to the next AED 100 self-test activation time, based upon the start of the sensed second sensor 318 output, such as a periodic informational IRDA message output.

After performing the above method steps, monitoring device 300 returns to a low-power standby mode of operation at entering low-power standby mode step 714, and awaits the next scheduled activating step 704. The method may end at step 716 if the AED and/or monitoring device 300 is taken out of service.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the scope of the appended claims.

What is claimed is:

1. A monitoring device for sensing an operating status of a defibrillator having an audible annunciator with a diaphragm, comprising:
   a sensor disposed adjacent the annunciator and operable to detect a non-audible parameter related to a diaphragm motion of the annunciator diaphragm;
   a hardware processor in electrical communication with the sensor;
   a comparator in communication with the hardware processor;
   a non-transitory computer storage medium in communication with the comparator and the hardware processor, wherein the medium is arranged to store a known characteristic of the annunciator,
   wherein the comparator compares the non-audible parameter to the known characteristic to confirm the sensor detection, and
   an output in communication with the hardware processor for providing a signal indicative of the diaphragm motion.

2. The monitoring device of claim 1, wherein the sensor comprises a capacitive sensor.

3. The monitoring device of claim 2, further comprising an electrically conductive decal adhered to the defibrillator on a defibrillator surface adjacent the annunciator, wherein the sensor is disposed to detect an annunciator-induced vibration of the defibrillator surface.

4. The monitoring device of claim 1, wherein the sensor comprises a temperature sensor, and wherein the parameter is a temperature change induced by the motion of the diaphragm.

5. The monitoring device of claim 1, wherein the sensor comprises an optical sensor, wherein the optical sensor is disposed to detect a change in reflectance of the diaphragm during the diaphragm motion.

6. The monitoring device of claim 1, wherein the sensor comprises an optical sensor and further comprising an optically reflective decal adhered to the defibrillator on a defibrillator surface adjacent the annunciator, wherein the optical sensor is disposed to detect an annunciator-induced vibration of the defibrillator surface.

7. The monitoring device of claim 1, wherein the sensor comprises an accelerometer that is arranged to detect an annunciator-induced vibration of the defibrillator surface.

8. The monitoring device of claim 1, further comprising a low-power standby circuit with a clock, the low power standby circuit in communication with the hardware processor and operable to activate the hardware processor for a predetermined time on a predetermined periodicity.

9. The monitoring device of claim 8, wherein the predetermined periodicity corresponds to a self-testing periodicity of the defibrillator.

10. The monitoring device of claim 9, further comprising a second sensor in communication with the hardware controller, the second sensor operable to sense one of a wireless data communication and an infrared data communication (IRDA) output from the defibrillator, wherein the hardware processor is operable to adjust the predetermined periodicity based on the sensed output from the defibrillator.

11. The monitoring device of claim 8, wherein the hardware processor enters a low-power standby mode of operation after the predetermined time.

12. The monitoring device of claim 1, further comprising a computer storage memory in communication with the hardware processor and the output, wherein the computer storage memory stores data indicative of the sensor detection.

13. The monitoring device of claim 12, wherein the data indicative of the sensor detection comprises a number of operations of the diaphragm.

14. The monitoring device of claim 1, wherein the known characteristic is one of a diaphragm operating frequency, a diaphragm operating duration, and a diaphragm temperature change resulting from the motion of the diaphragm.

15. A method of sensing an operating status of a defibrillator having an audible annunciator with a diaphragm, comprising the steps of:
   providing a monitoring device disposed adjacent the defibrillator, the monitoring device including a sensor disposed adjacent the annunciator and operable to detect a non-audible parameter related to a motion of the diaphragm, a hardware processor in electrical communication with the sensor, and an output in communication with the hardware processor for providing a signal indicative of the diaphragm motion;
   sensing with the monitoring device a motion of the annunciator diaphragm;
   comparing the motion from the sensing step with a known characteristic of the annunciator diaphragm, and
   generating an output signal responsive to the comparing step.

16. The method of claim 15, wherein the known characteristic is one of a diaphragm operating frequency, a diaphragm operating duration, and a temperature change resulting from a diaphragm operation.

17. The method of claim 15, further comprising a step of transmitting a wireless communications signal from the monitoring device to a remote receiver responsive to the generating step.

18. The method of claim 15, further comprising the steps of:
   activating the monitoring device on a predetermined schedule prior to the sensing step; and
   entering a low-power standby mode of operation after the sensing step.

* * * * *